United States Patent [19]

Luther et al.

[11] Patent Number: 4,950,256
[45] Date of Patent: Aug. 21, 1990

[54] NON-THROMBOGENIC INTRAVASCULAR TIME RELEASE CATHETER

[75] Inventors: Ronald B. Luther, Newport Beach; Edward Shanbrom, Santa Ana, both of Calif.

[73] Assignee: Luther Medical Products, Inc., Tustin, Calif.

[21] Appl. No.: 462,911

[22] Filed: Jan. 11, 1990

Related U.S. Application Data

[63] Continuation of Ser. No. 178,621, Apr. 7, 1988, abandoned.

[51] Int. Cl.$^5$ ............................................. A61M 5/325
[52] U.S. Cl. .................................................... 604/265
[58] Field of Search ................................. 604/265, 266

[56] References Cited

U.S. PATENT DOCUMENTS

| | | | |
|---|---|---|---|
| 3,987,797 | 10/1976 | Stephenson | 128/335.5 |
| 4,642,104 | 2/1987 | Sakamoto et al. | 604/265 |
| 4,704,102 | 11/1987 | Guthery | 604/28 |
| 4,723,950 | 2/1988 | Lee | 604/322 |
| 4,749,585 | 6/1988 | Greco et al. | 623/12 |

*Primary Examiner*—Stephen C. Pellegrino
*Assistant Examiner*—Sharon Rose
*Attorney, Agent, or Firm*—Grant L. Hubbard

[57] ABSTRACT

An intravascular catheter comprising a cannula for insertion into a vascular system of a patient coated with hydrophilic polymer containing, in the polymer, an effective amount of polymyxin to prevent the growth of microorganisms is disclosed.

1 Claim, No Drawings

NON-THROMBOGENIC INTRAVASCULAR TIME RELEASE CATHETER

This is a continuation of co-pending application Ser. No. 178,621, filed on Apr. 7, 1988, now abandoned.

Field of the Invention

This invention relates to in-dwelling intravascular catheters.

BACKGROUND OF THE INVENTION

Blood compatibility is much more complex than the compatibility of a biomaterial with other body fluids or tissues. The extent of the compatibility of blood with a specific biomaterial depends on whether the blood is moving (as in a heart device or blood vessel) or static (as in a storage bag or bottle); whether the blood is arterial or venous; flow patterns and especially changes in flow patterns; and interactions with red cells, white cells, platelets, plasma proteins and other blood components. Blood is a heterogeneous, non-Newtonian fluid consisting of about 45% solids (red cells, white cells, platelets) and 55% plasma. The plasma contains a variety of inorganic ions and a series of soluble proteins which can be classified as albumins, fibrinogens, and globulins.

Blood forms a clot or thrombus when injury occurs or when it is contacted by a foreign substance. Almost all biomaterials set off this clot-formation process and soon become coated with an irreversible clot of varying size that could have an adverse effect on the utility of the biomedical device and even be fatal to the patient. Blood compatibility of certain hydrophobic polymers, such as polydimethylsiloxane and the polyether polyurethane ureas (PEUU) is inversely related to the wettability of the polymers. But certain hydrophilic polymers, such as hydrogels, are also blood compatible. Certain ionomer-type polymers and electrets (charged polymers) are also compatible with blood. Blood compatibility is, to some extent, related to the nature of the proteins that adsorb on the biomaterial surface. Whenever the blood contacts a foreign surface various plasma proteins adsorb on this surface. Within some classes of polymers, such as hydrophobic polyether polyurethane ureas and the hydrophilic hydrogels, surfaces that adsorb mostly cold insoluble globulins (fibronectin) and fibrinogen tend to be more thrombogenic than those that adsorb albumin. Protein adsorption is a slow process, requiring many hours or days, whereas thrombus formation begins in a matter of minutes. Thus, some biomaterials show initial thromboresistance but develop clots after several weeks, possibly because of changes in the adsorbed protein layer. While various theories seem adequate to explain why one polymer in a given class is more or less blood compatible than another polymer of the same class, no theory is adequate to explain all the variations in blood compatibility for natural and synthetic materials.

A number of biomaterials have limited utility in various extracorporal devices if a suitable anticoagulant, such as heparin, is added to the blood. However, administration of heparin reduces or prevents the natural clotting of the blood. Heparin, a naturally occurring polyanionic mucopolysaccharide with a molecular weight of 12,000-16,000 has been attached to various surfaces by a variety of techniques. Although ionically bound heparin confers a significant degree of thromboresistance to the surface, the heparin desorbs and/or is inactivated with time and the basic thrombogenic nature of the surface prevails. Covalently bonded heparin maintains its thromboresistance longer, although the heparin is usually somewhat less active than the natural material. It appears likely that many experimental non-thrombogenic amido-amine polymers are thromboresistant because heparin is adsorbed at the amido-amine sites since many of the heparinization techniques involve a quaternary ammonium compound and heparin does form complexes with amino groups. Several experimental polymer systems have shown promise. These include the Ioplex materials and other hydrogels such as those based on 2-hydroxyethyl methacrylate or acrylamide. These materials may contain 50-80% water and it was claimed formerly that this was the basis of thromboresistance of hydrogels. More recent studies have shown that blood compatibility does not depend on the water content of hydrogels. Hydrogels normally lack physical or mechanical strength, a problem that has been partially solved by grafting hydrogels onto other substrates or by making a composite material with the hydrogel surface contacting the blood. Various lysing agents, such as urokinase or streptokinase, have been bonded to polymers with the intention of lysing any clotted material that might form on the surface. Certain polyether polyurethane ureas (PEUU) show good thromboresistance and are generally regarded as promising materials for internal use. The PEUU system, can be made with a wide variety of alkyl and/or aryl polymer groups and is often referred to as a segmented polyurethane. Devices made from these hydrophobic polymers often show no evidence of thrombus build up on the surface, but emboli are noted in other parts of the test animal's body.

Notwithstanding the great advances in materials sciences, in the understanding of the clotting process and its relationship to various materials, in bactericides, viricides and fungicides, one of the major hazards of modern medical practice, especially inhospital practice, is the risk of thrombus formation and infection associated with intravascular invasive devices, all classes and types of which are referred to here for convenience as catheters. The principal feature and object of this invention is to provide an improved catheter which significantly reduces the risk of infection and, at the same time, reduces the risk of thrombus and embolus formation.

Born into an environment laden with microbes, the body of man becomes infected from the moment of birth. Throughout life the skin and mucous membranes, exposed to the outside world, harbor a variety of bacterial, fungal and viral species, many of which establish more or less permanent residence on and in the superficial tissue. Some species cause no overt disturbance, some are symbiotic with man, some are essential to man's continued existence, and some place man's future health and life at risk. Some species may be inoffensive on the skin but become pathogenic in the blood stream. Some species may be nonpathogenic or so weakly pathogenic that they have no effect upon a healthy body with a strong immunological defense, but may become mildly or even fatally pathogenic in a body weakened by age, disease, radiation, chemotherapy or even by mental and emotional depression.

As more people with major diseases receive better treatment and thus live longer, and yet suffer from small or great debilitation of the immune system from the major disease or its treatment, and as more infections caused by virulent exogenous organisms are controlled by effective antimicrobial drugs, endogenous bacterial and other microbial diseases have become more common. Such diseases now constitute a major proportion of the serious bacterial diseases encountered in clinical practice.

The dramatic increase in the use of vascular invasive devices and the ready availability of a vast array of catheters and other such devices of new materials, have introduced higher risk factors to both the patient and the medical practitioner. Some of the problems springing from this phenomena are described in a communication "Plastic Devices: New Fields for Old Microbes", *The Lancet*, p. 365, Feb. 13, 1988.

The bacterial flora found on human skin varies in degree and variety depending on which part of the skin is examined. A typical skin bacterial flora will include Staphylococci, *Streptococci viridans, Streptococci-faecalis*, Corynebacteria, and Mycobacteria, and may, depending upon which skin area is examined, include Pneumococci, Clostridia, *Enteric bacilli*, spirochetes, Mycoplasmas, *Streptococci anaerobic*, as well as other species. Fungi such as the yeasts, Candida, *C. albicans* especially, is frequently a constituent of skin or membrane flora.

Among the most common, and potentially most serious, pathogens frequently found on the skin are the Staphylococci. Staphylococci are spherical, grampositive organisms which cause a wide variety of suppurative diseases in man. Because staphylococci frequently become drug-resistant, they have risen to a position of special significance in clinical medicine.

Man is constantly exposed to staphylococci. The skin and nose of the infant are colonized within a few days of birth. *S. epidermidia* is a virtually constant inhabitant of the human skin and mucous membranes. Infection of the skin, nose, oropharynx and intestinal tract with *S. aureus* is common. So long as the skin remains unbroken, large colonies of staphylococci may, and do, inhabit the skin without any adverse effect. A wound, a burn or any other breaking of the skin, however, invites infection.

One of the major problems in the use of intravascular catheters and in the control of infections during hospitalization is the tendency of some bacteria, such as *Staph. epidermidis*, for example, to mutate when challenged with antibiotics to produced a strain which is resistant to the antibiotic. Thus, infection control techniques which rely upon traditional antibiotic treatment tend to be only temporarily effective. Staph. and other infectious organisms are not known to mutate or form strains which are resistant to polymyxin. It is possible, but not known for certain, that such resistance is not developed toward polymyxin B because it is an outer membrane-disorganizing agent which lyses and inactivates the organism rather than attacking internally. Thus, it is believed, the organism is destroyed without triggering the mutation-protection mechanism which is inherent in some bacteria.

The prior art includes many needles, catheters and other devices for insertion into the body. The present invention is suitable for use with and may comprise as an element or as elements thereof such devices. For example, the assembly of breakaway needle and catheter is disclosed by , Luther et al in U.S. Pat. No. 4702735, who also disclose the assembly of stylet and catheter, Luther, U.S. Pat. Nos. 4668221 and 4610671, the assembly of stylet and catheter, Luther, U.S. Pat. No. 4610671, the assembly with septum fitting for connecting adaptor and fluid tube, Luther et al, U.S. Pat. No. 4559043, a small gauge, pre-split cannula and process for manufacture, Luther e al, U.S. Pat. No. 4449973, apparatus for advancing oversized catheter through cannula, and the like, Luther, U.S. Pat. No. 4401433, and cannula needle for catheter, Frey et al, U.S. Pat. No. 4377165.

The use of a hydrophilic polymer in connection with, as a coating for, or as a component of medical devices is well known in the art. It is also well known to use such polymers as reservoirs of drugs, antibiotics, etc. for time release devices while they are in-dwelling in the body. The assembly of stylet and catheter described by Luther in U.S. Pat. No. 4610671, for example, includes the description of a catheter which is constructed of a hydrophilic polymer which expands away from the stylet and permits the stylet to be withdrawn from the puncture site, leaving the catheter in place in the vein and a method of inserting an assembly of an over-the-stylet catheter into a puncture site in a vein, artery or the like, without coring which utilizes such a catheter.

An isocyanate cured coating articles for insertion into the body is described by Lambert in U.S. Pat. Nos. 4666437 and 4585666 for coating a polymer surface with a hydrophilic coating with low friction in wet condition. The process comprises applying to the polymer surface a solution containing a compound which comprises at least two unreacted isocyanate groups per molecule, evaporating the solvent, applying a solution containing polyvinylpyrrolidone to the thus treated polymer surface and curing the coating in the presence of a catalyst for the curing of isocyanate.

A method of applying a hydrophilic coating to a polymeric substrate and articles prepared thereby which includes desolventizing by evaporation a coating of polyvinylpyrrolidone to give surface lubricity when wet with water is described by Graper et al, U.S. Pat. No. 4589873.

Medical tubing having exterior hydrophilic coating for microbicide absorption therein and method for using same are described by Norton, U.S. Pat. No. 4515593. This catheter or the like has a body portion formed of a hydrophobic elastomer and a predetermined selected portion of the exterior surface intermediate the ends coated with a hydrophilic elastomer for reception of a microbicide along a limited portion at the cite of the entry of the catheter into the body.

An infusion device intended for implantation in a living body is disclosed by Franetzki et al, U.S. Pat. No. 4511355 which may include a hydrophilic diaphragm.

A medical article, catheters for example, having a hydrophilic coating; polyetherurethane copolymers are disclosed in U.S. Pat. Nos. 4487808 and 4459317. The process comprises applying to the polymer surface a solution containing a compound which has at least two unreacted isocyanate groups per molecule, evaporating the solvent, applying a solution of polyethylene oxide.

A catheter with a hydrophilic plastic casing is taught by Torsten, U.S. Pat. No. 4434797. The catheter is made of plastic provided with an outer casing which entirely or partially covers the catheter and consists of a hydrophilic plastic substance capable of absorbing liquid and thereby to increase its volume, i.e. To swell, so that the catheter maintains its position after its insertion into a body duct, vessel or cavity.

A gas sensor catheter with ph-sensitive FET transducer for measuring blood carbon dioxide concentration is taught by Shibatani et al, U.S. Pat. No. 4409980. A hydrophilic polymer layer extends over both said gate region of the FET transducer, the reference electrode and electrolyte which is sensitive to variations in hydrogen ion concentration.

A releasable balloon catheter is disclosed by Hajime, et al, U.S. Pat. No. 4346712, in which the catheter body comprises a hydrophilic polymer.

Polyurethane polyene compositions suitable for use in the present invention, and constituting a preferred hydrophilic polymer, are taught by Gould et al in U.S. Pat. Nos. 4359558, 4408023, 4439583, 4439584, 4439585, 4451635, 4454309, 4490423, and 4496535. Generally speaking, these patents relate to shaped three-dimensional structures formed of polyurethane polyene compositions obtained by reacting from about 10 to about 50 parts by weight of a polyene in the presence of about 100 parts by weight of a hydrophilic polyurethane resin. The resulting products will swell and increase in weight upon immersion in water and are permeable to gases, moisture vapor, ions, and other low molecular weight species. The hydrophilic polyurethane polyene compositions may be molded to form shaped products that are dimensionally stable after repeated exposure to boiling water and exhibit memory. Specific disclosures are also included. For example, three-dimensional substrates having on at least one surface a coating formed of a polyurethane polyene composition obtained by reacting a polyene in the presence a hydrophilic polyurethane resin are disclosed. Addition-condensation polymers of allyl or acrylic esters for applications such as contact lenses and medical equipment of polyurethane polyene compositions are obtained by reacting polyene in the presence hydrophilic polyurethane resin. Polyurethane quaternary ammonium salts are obtained by heating a solution of a polyurethane resin having polymer backbone hydroxyl groups and a compound having carboxylate radicals or carboxyl radicals, adding a strong base to the reaction mixture and continuing to react the mixture to form a polyurethane quaternary ammonium hydroxide in solution. The polyurethane quaternary ammonium hydroxide is recovered by pouring the reaction mixture into an excess of water. The polyurethane quaternary ammonium hydroxide so obtained may be dissolved in a solvent containing sufficient hydrochloric acid to bring the ph of the solution to 8; and the corresponding polyurethane quaternary ammonium chloride may be recovered from solution by evaporation. A polyurethane quaternary ammonium sulfate may be prepared by dissolving in sulfuric acid a polyurethane resin having polymer backbone hydroxyl groups and lactone groups. This solution is added to an excess of water with stirring and neutralized with sodium hydroxide to bring the ph of the diluted solution to between 3 and 4. Evaporation of the solvent gives a residue containing a polyurethane quaternary ammonium sulfate and sodium sulfate. The polyurethane quaternary ammonium sulfate may be separated from the mixture by extraction with methanol. Polyurethane diacrylate compositions are obtained by reacting a diacrylate in the presence of a hydrophilic polyurethane resin. The compositions will form a hydrogel upon immersion in water and are permeable to gases, ions and other low molecular weight species. The compositions are useful as carriers for pharmacologically active agents in forming an oral delivery system. Gas and ion permeable membranes useful as burn dressings, surgical drapes and the like formed of polyurethane diacrylate compositions obtained by reacting a diacrylate in the presence of a hydrophilic polyurethane resin. The compositions will form a hydrogel upon immersion in water and are also permeable to other low molecular weight species. Canulae may be formed of or have a coating of polyurethane diacrylate compositions obtained by reacting a diacrylate in the presence of a hydrophilic polyurethane resin. Surgical implants, intrauterine devices and the like formed of polyurethane diacrylate compositions obtained by reacting a diacrylate a hydrophilic polyurethane resin. The shaped products contain distributed therein a desired medicament. These compositions are useful for making contact lenses and numerous forms of surgical devices, among other things.

Peptide antibiotics produced by Bacillus species include several that are chemically closely related although produced by taxonomically different species: bacitracin from *Bacillus licheniformis* and *Bacillus subtillis* and polymyxins from *Bacillus polymyxa, Bacillus aerosporus, Bacillus colistinus,* and *Bacillus circulans*. Of this class of antibiotics, the subclass of antibiotics of principal, but not exclusive, interest in this invention are the Polymyxins. Polymyxins are antibiotics with a detergent like action, containing basic groups of the amino acid $\alpha,\gamma$-diaminobutyrate plus a fatty acid side chain, which destroys the integrity of the membranes of gram-negative but commonly thought not to effect gram-positive bacteria. Because of their neuro- and nephrotoxicity the use of polymyxins is limited to serious infections caused by susceptible organisms which have built up resistance to or have natural resistance to other biocidal materials. Polymyxins are, for example, among the few drugs effective against *Pseudomonas aeruginosa* which is a frequent and persistent secondary invader in patients under prolonged chemotherapy. The polymyxins inhibit the growth of a number of gram-negative organisms including Pseudomonas, Escherichia, Klebsiella, Enterobacter, Salmonella, Shigella, and Haemophilus species and are not inhibitors of growth of Proteus and gram-positive bacteria. Preparations of sulfates of polymyxin B and of colistin (polymyxin E) are used for local, topical, oral, and intravenous medication, and the sodium N-sulfomethyl derivatives are used for intramuscular and intrathecal administration. A wide range of mixed antibiotic formulations is marketed.

Ainsworth and co-workers, Shepherd and co-workers, and Benedict and Langlykke announced in 1947 aerosporin and polymyxin from *Bacillus polymyxa* strains. This led to an understanding that a group of closely related antibiotics of interest here referred to by the generic name polymyxin. Aerosporin was renamed polymyxin A and polymyxin became polymyxin D. Both of these antibiotics were nephrotoxic and this clinical defect led to the search for other antibiotic-producing strains of *B. polymyxa* and the development of four new polymyxins B, C, E, and F. Polymyxins B and E produced negligible toxic effects within the limits of the therapeutic dosage rang. Other polymyxins were discovered during evaluation of other strains of *Bacillus polymyxa*. Examples are the class of antibiotics known as colistin from a microorganism initially identified as a strain of *Bacillus colistinus* and now classified *Bacillus polymyxa* var. *garyphalus* and a strain of *B. polymyxa* from a soil sample taken in Moscow yielded an antibiotic which was designated as polymyxin M. *Bacillus brevis* produces an antibiotic mixture of which tyrothricin is a major constituent. *J. Boil. Chem.* 141:155, 163 (1941). Tyrothricin has been separated into three quite well known cationic cyclic polypeptide antibiotics, Tyrocidine A, B, and C. Other cationic cyclic polypeptide antibiotics, which are presently considered equivalent include the gramicidins, viomycins, capreomycins. Cationic cyclic polypeptide antibiotics, of which the polymyxins are the best known and including the colistins, gramicidins, viomycins, capreomycins and tyrothricins, are useful in the present invention; Polymyxin B, being used in what is presently considered the best mode of carrying out the invention. Because the polymyxins are the best known, the term "polymyxin" as used here will, unless specified differently, means the general family of polymyxins and the equivalent, related cationic cyclic polypeptide antibiotics, the specific species Polymyxin B being the preferred compound.

All of the polymyxins are basic polypeptides whose basicities are associated with the uncommon basic amino acid, $\alpha,\gamma$-diaminobutyric acid. They form water-soluble salts with mineral acids with only the phosphates being isolated in crystalline form. The normal form of pharmaceutical presentation of the sulfates and the hydrochlorides is amorphous solids. The water insolubility of the naphthalene-2-sulfonates and azobenzene-4-sulfonates is of advantage in purification of the polymyxins and crystalline forms can be obtained from aqueous alcohols. The picrates, reineckates, helianthates, Polar Yellow and other acid dyestuff salts, long-chain alkyl sulfates, etc, are very insoluble in water and are useful in the various purification procedures.

Intramuscular injection of polymyxins is painful and tends to result in an inflammatory reaction at the site of injection.

When polymyxins are treated with formaldehyde and sodium bisulfite they are converted into their sodium N-sulfomethyl derivatives, which are relatively free from causing pain upon injection and still retain most of their antibacterial activities. The potency of these derivatives depends on regeneration in vivo to the parent compound so the nephrotoxicity is not significantly reduced. The degree of N-sulfomethylation varies: most preparations of Coli-Mycin have about 50% of the maximum 7 sulfomethyl groups.

Polymyxins A and D each contain two D-amino acid residues, while polymyxins B and E have one. This difference may be responsible for the higher nephrotoxicity with the A and D compounds. The higher proportions of hydroxyamino acids found in A and D are reflected in the water solubility of the bases of these polymyxins, in contrast with that of polymyxins B and E and circulin A, which precipitate when aqueous solutions are neutralized.

The sulfates of polymyxin B and colistin have been used orally for gastrointestinal infections and bowel sterilization prior to surgery, but because of poor absorption, they are not used for systemic infections.

Tyrocidine A, Tyrocidine B and Tyrocidine C are closely related polypeptides which are known to possess antimicrobial action comparable to that of the better known Polymyxin B.

Polymyxin B in isotonic saline (0.5%) is used intrathecally and sterile, pyrogen-free polymyxin B sulfate is available for intravenous infusion in cases of severe systemic infection (usually requiring hospitalization). Although the acute intravenous toxicity is reduced by sulfomethylation with formaldehyde and sodium metabisulfite, this toxicity is of little therapeutic importance because the polymyxin B sulfates have a satisfactory therapeutic index. The main advantage of the sulfomethyl derivatives is the reduction of pain at the site of intramuscular injection and thus making parenteral therapy tolerable to the patient. A correlation of the intravenous LD50 values of various preparations and their therapeutic efficiency has been observed. The data showed that detoxification by sulfomethylation is minimal and that derivatives with LD50 (iv in mice) of the order of 100 mg/kg are a reasonable compromise. Polymyxins are useful when administered intramuscularly or intrathecally to combat acute enteritis, urinary and respiratory tract infections, bacteremia, peritonitis, and meningitis caused by *Pseudomonas sp Escherichia coli, Enterobacter aerogenes,* and *Klebsiella sp.*

An endotoxin detoxifying process which includes contacting blood with fibrous carrier having Polymyxin fixed thereon is disclosed by Hanazawa Kazuyoshi, et al, U.S. Pat. No. 4661260.The endotoxin detoxifying material comprising a fibrous carrier to which Polymyxin is fixed. A method of removing endotoxin from a fluid by contacting the fluid with the endotoxin detoxifying material comprising a carrier to which Polymyxin is fixed is also disclosed. The disclosed method it possible to contact blood with polymyxin directly and safely and gives a new method of therapy of endotoxemia or prophylaxis of endotoxemia, and compounds for use in antibacterial therapy are disclosed by Vaara Martti in U.S. Pat. No. 4510132.

Notwithstanding the long usage of polymyxins in a great variety of applications, the risks associated with the insertion of in-dwelling intravascular catheters has not been greatly reduced for many years. It is, therefor, an object of this invention to provide a catheter which not only reduces the frequency and seriousness of thrombus or embolus formation but also greatly reduces the risk of infection at the site of the invasion of the body by the catheter and in the vascular system.

SUMMARY OF THE INVENTION

The present invention comprises an intravascular catheter comprising a cannula constructed and dimensioned for insertion into an vascular system of a patient. Typically, but not necessarily, the catheter includes or comprises a cannula. If the catheter includes a cannula, a coating of hydrophilic polymer is applied on the cannula. If a non-cannulated catheter is used, then the coating is on the outside of the catheter. A cationic cyclic polypeptide antibiotic, e.g. the polymyxins, Polymyxin B being used in what is presently considered the best mode of carrying out the invention, is introduced into the hydrophilic polymer coating sufficient to be effective to substantially prevent the growth of polymyxin-sensitive microorganisms and to inhibit thrombus formation on the catheter.

The advantageous and unexpected features of this invention include the discovery that providing a level of cationic cyclic polypeptide antibiotics, of which the polymyxins are the best presently known examples, in or on the surface of a catheter not only inhibits the growth of pathogenic gram negative bacteria, but also inhibits the growth of gram positive bacteria, inhibits the replication of virus, inhibits the growth of fungal infection sites, prevents the development of tolerance to the antibiotic, and creates a non-thrombogenic surface on the catheter.

DESCRIPTION OF THE PREFERRED EMBODIMENT

The present invention relates to a device designed and intended to remain in contact with blood, either in blood vessels or in incisions, for a period of time. The most important embodiment of the invention, commercially, is considered to be an intravascular catheter constructed and dimensioned for insertion into an vascular system of a patient, coated hydrophilic polymer in any desired thickness treated by dipping, spraying or other application techniques with cationic cyclic polypeptide antibiotics, of which the polymyxins are the best presently known examples.

Invasive devices for dwelling in contact with fibrinogen-fibrin containing fluid of a patient which contains fibrinogen-fibrin capable of forming clots generally are within the contemplated applications of the present process and invention. Such devices would include, for example, tubes introducing medication into or draining fluid from hydrencephaloceles and cavities in connection with the treatment of pleurisy and peritonitus and other diseases and infections, and in similar applications where it is important to avoid fibrin deposition and clotting are included within the devices referred to herein. The principal applications being, of course, vascular devices such as catheters. An invasive device for dwelling in contact with fibrinogen-fibrin containing fluid of a patient comprising a structure constructed and dimensioned for insertion into a patient for residing in contact with a fluid in the patient which contains fibrinogen-fibrin capable of forming clots A convenient method of preparation of the catheters of this invention is to dip catheters of the type described in the Luther et al patents, supra, in an aqueous or alcoholic solution of the cationic cyclic polypeptide antibiotic. Other solvents may, of course, be used but the hydrophilic nature of the coating on these catheters makes an aqueous solution of the antibiotic nearly ideal. Solutions of from 0.1 percent (by weight) to a saturated solution, approximately 50 $^w/o$, may be used. Solutions in the range of about one weight percent in concentration have been found most convenient. Cationic cyclic polypeptide antibiotic, e.g polymyxin, are thus introduced into the hydrophilic coating in amount which is determined empirically to be effective to substantially prevent the growth of polymyxin-sensitive microorganisms and to inhibit thrombus formation on the catheter. The precise parameters as to the amount of the antibiotic in the polymer necessary to achieve this result have not been determined, nor are these parameters critical. Emersion of a hydrophilic polymer coated or treated catheter in a 1 $^w/o$ solution of Polymyxin B for a few minutes, e.g. from one or two minutes if the polymer is dehydrated up to a quarter to half an hour if the polymer is full hydrated is sufficient to accomplish the necessary loading of the cationic cyclic polypeptide antibiotic into the polymer.

As indicated, the thickness of the hydrophilic polymer is not critical insofar as this invention is concerned, and the thickness is determined on the basis of the mechanical characteristics and size limitations of the catheter per se.

Polyurethane polyene compositions preferred for use in the present invention are the hydrophilic polymers taught by Gould et al in U.S. Pat. Nos. 4359558, 4408023, 4439583, 4439584, 4439585, 4451635, 4454309, 4490423, and 4496535. Generally speaking, these patents relate to shaped three-dimensional structures formed of polyurethane polyene compositions obtained by reacting from about 10 to about 50 parts by weight of a polyene in the presence of about 100 parts by weight of a hydrophilic polyurethane resin. The resulting products will swell and increase in weight upon immersion in water and are permeable to gases, moisture vapor, ions, and other low molecular weight species. The hydrophilic polyurethane polyene compositions may be molded to form shaped products that are dimensionally stable after repeated exposure to boiling water and exhibit memory.

Other hydrophilic polymers may, however, be used effectively in the manufacture of the catheters of this invention.

As pointed out, several results which were not and could not have been expected have been discovered. These unexpected results include the discovery that providing a level of cationic cyclic polypeptide antibiotics, of which the polymyxins are the best presently known examples, in or on the surface of a catheter not only inhibits the growth of pathogenic gram negative bacteria, but also inhibits the growth of gram positive bacteria, inhibits the replication of virus, inhibits the growth of fungal infection sites, prevents the development of tolerance to the antibiotic, and creates a nonthrombogenic surface on the catheter.

The mechanism and chemistry by which these results are accomplished are not understood. Without being limited to any particular theory, it is believed likely that the anticoagulant action of cyclic polypeptides of this invention is related to the binding of thromboplastic and platelet phospholipids which are essential in clotting.

The nonthrombogenic surface effects resulting from the use of the cationic cyclic polypeptide antibiotics, of which the polymyxins are the best presently known examples, of this invention may be enhanced by the additional use of known anticoagulants such as heparin and chelating agents for calcium and magnesium, e.g. EDTA and citric acid.

A typical manufacturing process includes the steps of forming the catheter, by extrusion of a cannula of appropriate size for example, coating the catheter by dipping or spraying or otherwise applying one or a plurality of layers of hydrophilic polymer, and then applying the polymyxin B to the polymer, usually by dipping the catheter in a solution of polymyxin B, or passing the catheter through a bath or spray of such a solution.

The polymer may contain or be modified to include moieties or sites which can accept an electron pair and brought into contact with free (non-salt) polymyxin, which is basic, which will form a covalent bond with such moieties or sites.

Other anticoagulants, e.g. heparin, may be added also, and various chelating and other agents may also be included in the solution or added separately. Other specific antimicrobials may, for example, be included in the polymer, as is known in the prior art. Indeed, virtually any constituent which does not interfere with the described action of the cationic cyclic polypeptide antibiotics, of which the polymyxins are the best presently known examples, may be included in the polymer. Hence, the invention is described as a vascular invasive device of any kind which is used in contact with blood having a coating of a hydrophilic polymer containing an antimicrobial anticoagulant consisting essentially of cationic cyclic polypeptide antibiotics, of which the polymyxins are the best presently known examples.

The preferred form of the invention includes the polymyxin B, or other cationic cyclic polypeptide antibiotics, of which the polymyxins are the best presently known examples, in solution as a part of the aqueous component of the hydrophilic polymer. This embodiment provides a time-release mechanism which permits continuing renewal of the polymyxin B on the surface of hydrophilic polymer, and release of polymyxin B into the blood at a rate so low that the usual trauma and pain associated with polymyxin B is avoided. Virtually any concentration and any release rate can be attained by simple manufacturing techniques.

For example, if maximum uptake is desired, a dry or substantially dry hydrophilic polymer coating is saturated with aqueous solution of polymyxin B or a salt thereof, the concentration of the polymyxin solution being the principal determinant of the amount of polymyxin taken up in the polymer. Alternatively, a partially hydrolyzed polymer can be brought into contact with polymyxin B solution to limit the uptake of polymyxin B and to concentrate the polymyxin B near the surface of the hydrophilic polymer. Thus, concentration of the polymyxin B in the polymer is easily controlled by (a) controlling the concentration of polymyxin B in the solution and/or (b) controlling the amount of polymyxin B solution take into the polymer. By controlling these factors, virtually any desired concentration of polymyxin B in the hydrophilic polymer can be obtained, and the rate of time release controlled.

Catheters prepared as described herein were compared with the same type of catheter which differed only in the absence of the cationic cyclic polypeptide antibiotic treated surface. Both catheters were dipped in whole blood for various periods of time. In one such test, the catheters were compared for clotting after one hour in the blood. The catheters treated according to this invention were virtually free of blood on the outside, and were free-flowing and free of clots on the inside. An identical catheter, absent the cationic cyclic polypeptide, when removed from the blood was coated on the outside and plugged substantially or entirely on the inside. A representative sample of commercially available catheters were used as controls. In all instances, they were coated with blood clots and were fully or partially block inside the lumen.

While one would expect that a polymyxin B coating on a catheter would exhibit the usual microbicidal characteristics of polymyxin B, i.e. anti-gram-negative bactericidal effects, but would also expect that the pain and trauma associated with intravenous polymyxin B therapy would be exhibited. One would not expect or predict, however, that a catheter coated with polymyxin B containing hydrophilic polymer would also prevent the growth of gram-positive bacteria such as, for example, slime producing *Staphylococcus epidermidis*. Surprisingly, however, gram-positive bacterial infections, at least by some species of staphylococci, are prevented by using the polymyxin B containing hydrophilic polymer coated catheters of this invention.

Still more surprising was the discovery that the polymyxin B containing hydrophilic polymer coated catheters of this invention were very substantially less thrombogenic than identical catheters without the polymyxin B constituent.

There are several indirect advantages resulting from the use of the catheter's of this invention, in addition to the more startling direct advantages referred to. The catheters, when removed, are generally quite clean and free of the large clots and coating of blood which are normally found. The small amount of blood which remains coupled with the antimicrobial action of the coating reduces the risk of infection to medical works, e.g. nurses, doctors and technicians, the most serious of which is the risk of infection with the HIV (AIDS) virus.

Thus, the catheters of this invention exhibit a number of surprising and unpredictable characteristics, and accomplish results not previously accomplished, which greatly reduce the risks in using intravascular catheters.

INDUSTRIAL APPLICATION

This invention finds application in the medical device industry, in hospitals and in the practice of medicine generally.

What is claimed is:

1. An invasive device comprising a structure constructed and dimensioned for insertion into a patient for residing in contact with a fluid in the patient which contains fibrinogen-fibrin capable of forming clots, and a coating on the structure, said coating consisting essentially of three-dimensional polymer formed of polyurethane polyene compositions obtained by reacting from about 10 to about 50 parts by weight of a polyene in the presence of about 100 parts by weight of a hydrophilic polyurethane resin, said coating having absorbed therein an amount of antimicrobial anticoagulant consisting essentially of polymyxin in amount effective to inhibit growth of bacteria and the formation of blood clots on said coating.

* * * * *